United States Patent
Shanmugam et al.

(10) Patent No.: US 10,686,878 B2
(45) Date of Patent: Jun. 16, 2020

(54) METHOD AND DEVICE FOR MANAGING DISPLAY OF MULTIPLE DATA STREAMS

(71) Applicant: Pacesetter, Inc., Sunnyvale, CA (US)

(72) Inventors: Muthuvale Shanmugam, Sunnyvale, CA (US); Pulkit Bisen, Valencia, CA (US); Chao-Wen Young, Cupertino, CA (US); Yongjian Wu, Saratoga, CA (US); Lisbet Miller, Sylmar, CA (US); Xing Pei, Thousand Oaks, CA (US); Reza Shahandeh, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 381 days.

(21) Appl. No.: 15/474,494

(22) Filed: Mar. 30, 2017

(65) Prior Publication Data

US 2018/0288147 A1 Oct. 4, 2018

(51) Int. Cl.
*A61B 1/00* (2006.01)
*H04L 29/08* (2006.01)
(Continued)

(52) U.S. Cl.
CPC .......... *H04L 67/1095* (2013.01); *A61B 5/002* (2013.01); *A61B 5/0006* (2013.01);
(Continued)

(58) Field of Classification Search
CPC ....... A61B 5/00; A61B 5/0004; A61B 5/0006; A61B 5/002; A61B 5/0031; A61B 5/0402;
(Continued)

(56) References Cited

U.S. PATENT DOCUMENTS 4,791,936 A * 12/1988 Snell .................... A61B 5/0006
600/510
5,987,352 A * 11/1999 Klein .................... A61N 1/375
600/509

(Continued)

FOREIGN PATENT DOCUMENTS

EP         1245248      10/2002
WO       2011097312     8/2011

OTHER PUBLICATIONS

International Search Report and Written Opinion for PCT/US2018025094, dated Jul. 18, 2018.

*Primary Examiner* — Ahmed M Farah
(74) *Attorney, Agent, or Firm* — The Small Patent Law Group LLC; Dean D. Small

(57) ABSTRACT

Methods and systems are provided to manage display of cardiac signals. The methods and systems receive a first data steam along a first communications path conveyed with first throughput and receiving a second data stream along a second communications path transmitted with second throughput. The first and second throughputs are asynchronous with respect to one another. The first and second data streams carry cardiac signals sensed by external and implanted electrodes, respectively, for one or more common events. The methods and systems store data from the first and second data streams in first and second memory buffers. The methods and systems synchronize the data stored in the first and second memory buffers with one another by performing at least one of: temporally offsetting activation of the storing operation for the first and second data streams with respect to one another; or managing an amount of the data maintained in at least one of the first memory buffer or the second memory buffer. The methods and systems co-display cardiac signals associated with the first and second
(Continued)

data streams on a display by reading the data from the first and second memory buffers at a data display rate.

9 Claims, 5 Drawing Sheets

(51) Int. Cl.
  *A61B 5/044* (2006.01)
  *A61B 5/00* (2006.01)
  *A61N 1/365* (2006.01)
  *A61N 1/39* (2006.01)
  *A61N 1/372* (2006.01)

(52) U.S. Cl.
  CPC ............ *A61B 5/0031* (2013.01); *A61B 5/044* (2013.01); *A61B 5/742* (2013.01); *A61N 1/365* (2013.01); *A61N 1/37217* (2013.01); *A61N 1/37247* (2013.01); *A61N 1/37252* (2013.01); *A61N 1/3956* (2013.01)

(58) Field of Classification Search
  CPC ............ A61B 5/04021; A61B 5/04023; A61B 5/0408; A61B 5/0428; A61B 5/74; A61B 5/040742; A61N 1/365; A61N 1/368; A61N 1/36247; A61N 1/3956; A61N 1/3962
  USPC ....... 600/301, 373–377, 382, 481, 485, 486, 600/508–523
  See application file for complete search history.

(56) References Cited

U.S. PATENT DOCUMENTS

| | | | |
|---|---|---|---|
| 6,753,873 B2* | 6/2004 | Dixon | A61B 6/56 345/542 |
| 6,901,159 B2* | 5/2005 | Baertsch | A61B 6/00 250/370.09 |
| 6,904,124 B2* | 6/2005 | Staver | A61B 6/4233 378/15 |
| 7,076,520 B2 | 7/2006 | Nelson et al. | |
| 7,299,085 B2* | 11/2007 | Bergelson | A61B 5/0006 128/903 |
| 7,454,248 B2* | 11/2008 | Burrell | A61B 6/541 600/428 |
| 7,751,889 B1* | 7/2010 | Schecter | A61B 5/0031 600/10 |
| 7,791,470 B2* | 9/2010 | Karr | G01S 3/52 340/10.1 |
| 7,945,333 B2* | 5/2011 | Jacobson | A61N 1/3708 607/59 |
| 8,391,980 B2 | 3/2013 | Bornzin et al. | |
| 8,831,747 B1 | 9/2014 | Min et al. | |
| 8,934,963 B1 | 1/2015 | Farazi | |
| 9,044,610 B2 | 6/2015 | Rosenberg et al. | |
| 9,216,285 B1 | 12/2015 | Boling et al. | |
| 9,232,485 B2 | 1/2016 | Wu et al. | |
| 9,333,351 B2 | 5/2016 | Arnold et al. | |
| 2002/0082665 A1* | 6/2002 | Haller | A61N 1/37264 607/60 |
| 2002/0193846 A1* | 12/2002 | Pool | A61B 5/0006 607/60 |
| 2004/0215089 A1 | 10/2004 | Bergelson | |
| 2008/0021504 A1* | 1/2008 | McCabe | A61N 1/36114 607/9 |
| 2008/0188763 A1* | 8/2008 | John | A61B 5/0452 600/516 |
| 2011/0224750 A1* | 9/2011 | Scheiner | A61N 1/36114 607/17 |
| 2015/0157231 A1 | 6/2015 | Gillberg | |
| 2016/0022164 A1* | 1/2016 | Brockway | A61B 5/0452 600/509 |

* cited by examiner

METHOD AND DEVICE FOR MANAGING DISPLAY OF MULTIPLE DATA STREAMS

BACKGROUND

Embodiments of the present disclosure generally relate to methods and devices for managing display of cardiac signals, and more particularly to manage display of cardiac signals based on data received from two or more asynchronous communications paths.

A next generation cardiac rhythm management (CRM) implantable medical device (IMD) has been proposed that utilizes Bluetooth Low Energy (BLE) telemetry to communicate with external instruments, such as a bedside monitor and/or programmer. Recently, it has been proposed that the monitor or programmer be configured to provide a scrolling display of real-time data. The programmer/monitor may receive two types of real-time data for monitoring heart rhythm, one is surface Electrocardiogram (ECG) data and the other is electrogram (EGM) data. The ECG data are recorded from the patient's body through a directly attached lead, while the EGM data are processed by the IMD and transmitted wirelessly to the programmer/monitor.

However, difficulties arise when the monitor/programmer attempts to display the ECG and EGM data simultaneously and in real-time. Even though both types of real-time data (ECG and EGM) are generated at the same time from the heart, the ECG and EGM data follow different paths as the data travel from the patient to the monitor or programmer. The different paths introduce different delays that cause the ECG and EGM data to arrive at the monitor or programmer out-of-sync. If left un-corrected, the out-of-sync data are presented to the user at the display of the monitor/programmer out of sync. Misleading information may be presented on the display if the ECG and EGM data are not presented in a coherent in-synch manner.

The dyssynchrony of the ECG and EGM data becomes even more prevalent when utilizing Bluetooth technology to transmit the EGM data from the IMD to the monitor/programmer. An inherent characteristic of a BLE protocol is the transmission of data in short bursts, not in a constant stream. While the BLE protocol seeks to utilize a maximum available BLE bandwidth, the BLE protocol is not optimized to provide EGM data in a manner that affords a smooth in sync scrolling display of real-time EGM traces. Also, the IMD introduces a certain amount of processing delay to process the EGM data and a communications delay to transmit the EGM data to the external monitor or programmer. The processing and communications delay introduce some constant and some in-deterministic delays which will make the display of real-time EGM data delayed and staggered with reference to corresponding ECG data.

Conventional approaches experience design challenges that do not compensate for the various delays and do not convert the short bursts of EGM data into a constant stream of EGM data at a desired rate. Conventional approaches do not display ECG and EGM data synchronized in a manner that enables a clinician to perform proper diagnosis.

SUMMARY

In accordance with embodiments herein, a method is provided to manage display of cardiac signals. The method comprises receiving a first data steam along a first communications path conveyed with first throughput and receiving a second data stream along a second communications path transmitted with second throughput. The first and second throughputs are asynchronous with respect to one another. The first and second data streams carry cardiac signals sensed by external and implanted electrodes, respectively, for one or more common events. The method stores data from the first and second data streams in first and second memory buffers. The method synchronizes the data stored in the first and second memory buffers with one another by performing at least one of: temporally offsetting activation of the storing operation for the first and second data streams with respect to one another; or managing an amount of the data maintained in at least one of the first memory buffer or the second memory buffer. The method co-displays cardiac signals associated with the first and second data streams on a display by reading the data from the first and second memory buffers at a data display rate.

Optionally, the method further comprises managing a read-out rate at which the first and second data streams are read from the first and second memory buffers to adjust the data display rate. Optionally, the method comprises comparing an amount of data from the second data stream loaded into the second memory buffer with a size threshold of the second memory buffer; and adjusting the data display rate based on the comparing operation.

Optionally, the method performs the managing operation which further comprises determining when the first data stream overflows a trailing end of a main segment of the first memory buffer and removing a leading portion of the first data stream by an amount based on the overflow. Optionally, the overflow represents a last-in data subset of the first data stream that is stored in an overflow segment of the first memory buffer and the removing operation purges, as the leading portion, a first-out data subset of the first data stream from a leading end of the first memory buffer. The first-out data subset that is purged corresponds in length to a length of the last-in data subset that overflows into the overflow segment.

Optionally, the synchronizing operation performs the offsetting operation which includes offsetting activation of storage of the second data stream until after activation of storage of the first data stream by a predetermined processing offset that corresponds to a processing delay introduced along the second communications path. Optionally, the synchronizing operation performs the offsetting operation which includes filling a leading segment of the first memory buffer from the first data stream before activating the storing operation for the second data stream, the leading segment corresponds to a processing delay introduced along the second communications path. Optionally, the synchronizing operation performs the managing operation, in which the storing operation fills a main segment of the first memory buffer from the first data stream, the main segment corresponds to a maximum transmission delay from a last data exchange until a link over the second communications path is declared lost. Optionally, the synchronizing operation performs the managing operation, which includes continuing the storing operation until the second memory buffer is filled for a period of time corresponding to a connection supervision timeout that is set in accordance with a protocol utilized for transmission over the second communications path.

The first and second data streams may correspond to ECG data and EGM data sensed by different ECG and EGM electrodes coupled to the first and second sensing circuits, respectively, wherein the EGM data is conveyed along a wireless link within the second communications path. The second communications path may correspond to a Bluetooth low energy (BLE) wireless link.

In accordance with embodiments herein, a system is provided to manage a display of cardiac signals. The system comprises a first input to receive a first data steam along a first communications path conveyed in accordance with a first throughput and a second input to receive a second data stream along a second communications path transmitted in accordance with a second throughput. The first and second throughputs are asynchronous with respect to one another. The first and second data streams carry cardiac signals sensed by external and implanted electrodes, respectively, for one or more common events. The system includes memory to store data from the first and second data streams in first and second memory buffers. The system has one or more processors that, when executing program instructions, synchronize the data stored in the first and second memory buffers with one another. The processors perform synchronization by temporally offsetting activation of the storing operation for the first and second data streams with respect to one another and/or managing an amount of the data maintained in at least one of the first memory buffer or the second memory buffer. The system includes a display to co-display cardiac signals associated with the first and second data stream by reading the data from the first and second memory buffers at a data display rate.

Optionally, the system comprises a sensing circuit connected to the first input, the first input configured to be connected to one or more ECG leads having ECG electrodes to sense ECG data as the first data stream. Optionally, the system includes a receiver connected to the second input, the receiver configured to communicate with an IMD to receive EGM data as the second data stream from the IMD in accordance with a Bluetooth Low Energy transmission protocol. Optionally, the first throughput represents even and continuous bursts and wherein the second throughput represents intermittent bursts.

Optionally, the system compares an amount of data from the second data stream loaded into the second memory buffer with a size threshold of the second memory buffer and adjusts the data display rate based on the comparing operation.

Optionally, the synchronizing operation performs the managing operation. The method further comprises determining when the first data stream overflows a trailing end of a main segment of the first memory buffer and removing a leading portion of the first data stream by an amount based on the overflow. The overflow may represent a last-in data subset of the first data stream that is stored in an overflow segment of the first memory buffer. The removing operation purges, as the leading portion, a first-out data subset of the first data stream from a leading end of the first memory buffer, the first-out data subset that is purged corresponding in length to a length of the last-in data subset that overflows into the overflow segment.

Optionally, the synchronizing operation performs the offsetting operation which includes offsetting activation of storage of the second data stream until after activation of storage of the first data stream by a predetermined processing offset that corresponds to a processing delay introduced along the second communications path. Optionally, the synchronizing operation performs the offsetting operation which includes filling a leading segment of the first memory buffer from the first data stream before activating the storing operation for the second data stream, the leading segment corresponding to a processing delay introduced along the second communications path.

DETAILED DESCRIPTION

Figure 1:
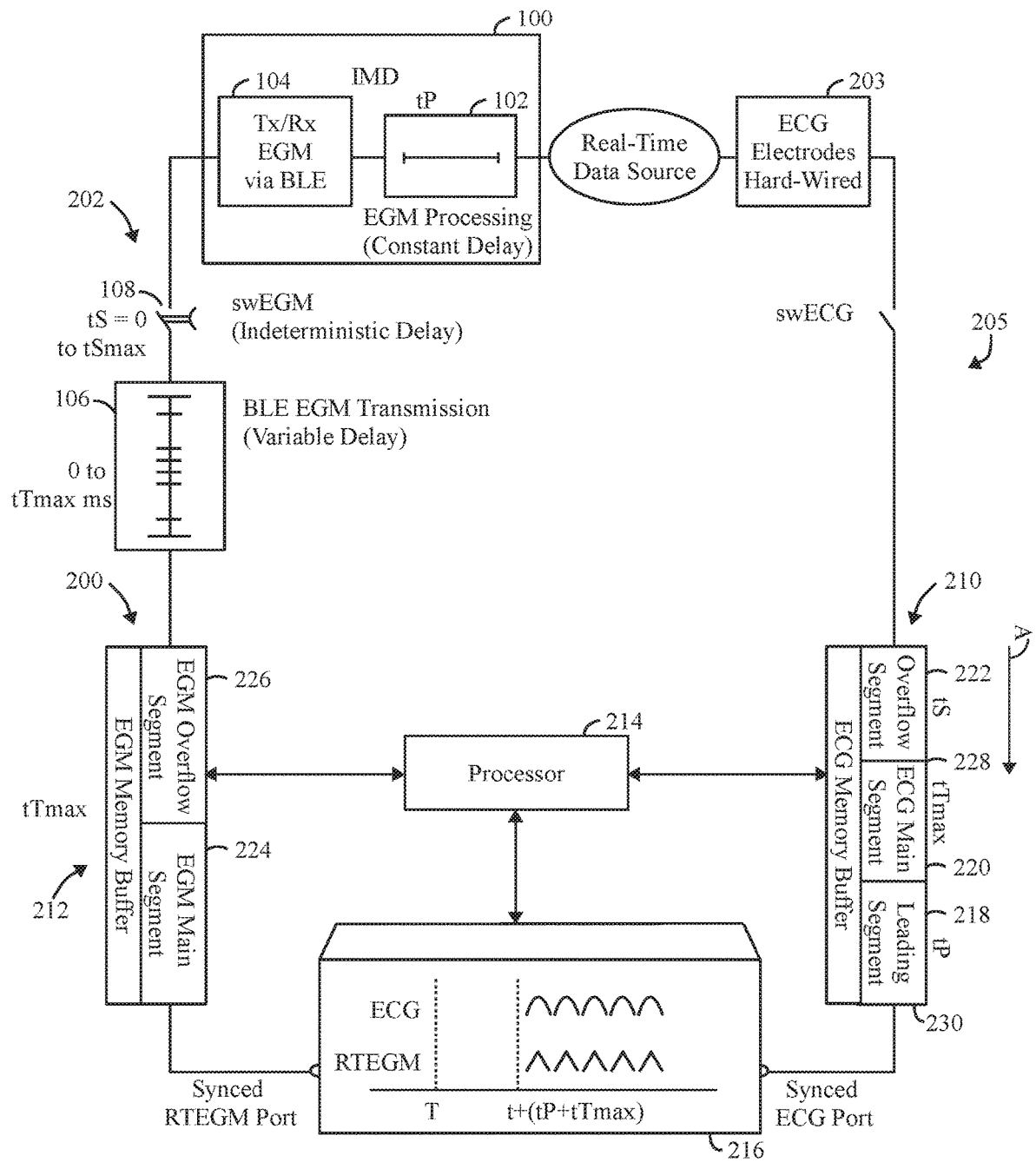
FIG. 1 illustrates a block diagram of a system formed in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Definitions

The term "memory buffer" is used to refer to a region of a physical memory storage used to temporarily store data while the data is being moved from one place to another. For example, the data is stored in a memory buffer as the data is retrieved from an input device (e.g., a lead, sensor, IMD) and/or just before the data is sent to an output device (e.g., a display, speakers). The buffer memory may be used when moving data between processes within a computer. Memory buffer can be implemented in a fixed memory location in hardware, or by using a virtual data buffer in software, pointing at a location in the physical memory.

The term "connection supervision timeout" refers to a timeout from a last data exchange until a link is considered lost. A central device (e.g., external device or IMD) will not start trying to reconnect before the timeout has passed.

The present specification describes embodiments that utilize certain time periods in connection with describing memory size or amounts of data stored in memory. For example, memory buffers and segments of memory buffers are described in connection with processing delay, transmission delay and the like. It should be recognized that memory size or amounts of data stored in memory at a point in time may be correlated to time periods based on data rates. For example, a data display rate (utilized to read out data from a buffer memory for display) may be utilized to determine an amount of data or a memory size for a given period of time. As another example, a maximum potential amount of data that may be transmitted in accordance with a communications protocol for a set period of time may be utilized to determine an amount of data or memory size that correlates with a given period of time. For example, when utilizing a BLE communications protocol, a maximum potential amount of data transmitted can be calculated for transmission during the "connection supervision timeout" interval. To the extent that embodiments herein describe the use of timers or timing thresholds, additionally or alternatively, the embodiments may substitute data or memory size of thresholds for such time or interval thresholds. To the extent that embodiments herein describe the use of data size thresholds or memory thresholds, additionally or alternatively, the embodiments may substitute timers or intervals for such size thresholds.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System," which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same," which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device," which are hereby incorporated by reference.

FIG. 1 illustrates a block diagram of a system formed in accordance with embodiments herein. The system includes an IMD 100 and an external device (ED) 200, such as a monitor or programmer. The IMD 100 may include one or more leads that are located proximate to a patient's heart. Optionally, the IMD 100 may be a leadless device. The IMD 100 senses cardiac signals at one or more implanted electrodes provided on the housing of the IMD 100 and/or on a lead. The sensed cardiac signals are associated with one or more paced or sensed cardiac events. The IMD 100 processes the sensed cardiac signals to form EGM data and transmits the EGM data over a wireless link to the ED 200. The EGM data is transmitted over an EGM communications path 202 in accordance with a wireless protocol. The wireless protocol defines a burst type of data transfer and thus the EGM data is transmitted with uneven throughput. For example, the wireless protocol may be the Bluetooth Low Energy (BLE) protocol, where the IMD 100 transmits EGM data in short bursts in an intermittent manner as defined by the BLE protocol. The ED 200 receives a stream of EGM data along the communications path 202 with a corresponding throughput.

The system also includes one or more leads with external surface electrodes 203 that are configured to be attached at corresponding positions on the patient's skin. The surface electrodes 203 sense cardiac signals associated with the same one or more paced or sensed cardiac events that are sensed at the implanted electrodes coupled to the IMD 100. The surface electrodes 203 sense the cardiac signals and convey associated ECG data to the ED 200. The ECG data is conveyed, as analog or digital data, from the surface electrodes 203 along an ECG communications path 205 with corresponding throughput.

The ED 200 includes a first/ECG memory buffer 210 and a second/EGM memory buffer 212 that are configured to store the ECG and EGM data streams under the control of one or more processors 214. The processors 214 manage storage of the ECG data and EGM data to the corresponding memory buffers 210, 212, as well as read out of the ECG and EGM data in connection with co-displaying cardiac signals on a display 216. The cardiac signals co-displayed are associated with the ECG and EGM data streams and are displayed at a data display rate that is managed by the processors 214 in accordance with embodiments herein. The processors 214 synchronize the ECG and EGM data streams with one another by performing at least one of various synchronization operations. As explained herein, one synchronization operation includes temporally offsetting activation of the storing operation for the ECG and EGM data with respect to one another. Additionally or alternatively, the synchronization operation includes managing an amount of the ECG data that is maintained in the ECG memory buffer based on various criteria.

In accordance with embodiments herein, the ED 200 buffers real-time ECG and EGM data in accordance with various criteria to compensate for various delays and to convert short bursts of the EGM data into a constant EGM data stream at a desired rate. The ED 200 displays ECG and EGM data temporally synchronized in a manner that enables a clinician to perform proper diagnosis. The methods and systems use a throttling technique to stream out smooth flowing synchronized EGM and ECG real-time data to a monitor or programmer display.

In accordance with embodiments herein, the methods and systems address various problems that can be separated into three distinct challenges, namely processing/transmission delay, startup command delay and batched data irregularity. The processing/transmission delay causes the EGM data to arrive inconsistently later than ECG data at the ED 200 even though both the EGM and ECG data originated at the same time from a common event (e.g., atrial or ventricular sensed or paced event). The processing delay is denoted graphically at 102 and represents a constant EGM processing delay within the IMD 100 between a sensing instance, when the EGM data is sensed at implantable electrodes, and a transmission instance, when the EGM data is transmitted from a transmitter 104 within the IMD 100. The transmission delay is represented graphically at 106 and will vary based on the transmission protocol. The transmission protocol represents a packet and burst type protocol, in which EGM data is grouped into packets and transmitted in bursts that are separated by intervals in which no EGM data is transmitted. When an EGM packet is received that includes errors, the EGM packet is retransmitted. The non-transmission intervals and retransmission of repeated EGM packets introduces unpredictable variable EGM transmission delays. The EGM transmission delay may also vary due to delays when establishing a wireless communications session and initiating EGM data transmission.

The startup command delay occurs because transmission of EGM data is switched on at a different instant in time than the instant in time at which the ECG data transmission is switched on (as noted graphically at 108). The difference in transmission start times causes the ECG and EGM data to arrive at the ED 200 out of sync from a start of a transmission. The start of EGM data transmission is delayed in part because the IMD 100 and ED 200 first establish a communication session there between, before the ED 200 can send a transmit data command to the IMD 100. The amount of time to establish the communications session and send the transmit data command varies and is unpredictable which causes an in-deterministic delay.

The batch data irregularity occurs because the EGM data is transmitted in batches as opposed to a continuous even stream. The batches of the EGM data arrive at the ED 200 in uneven short bursts, are stored in the EGM memory buffer 212, and then are read from the EGM memory buffer 212 for display on the display 216 in a continuous even manner in order to provide a smooth display. As explained herein, the EGM data may overflow the main segment of the EGM memory buffer 212 into an EGM overflow buffer 226.

In accordance with embodiments herein, methods and systems address the challenge of transmission delay of EGM data, in part, by temporally offsetting activation of storage of ECG data and activation of EGM data at the ED 200. For example, the ED 200 activates storage of the ECG data (e.g., turned on) first (before activation of storage of the EGM data). The ED 200 stores ECG data for a predetermined IMD processing delay that corresponds to the delay introduced along the second communications path as EGM data is sensed and processed within the IMD 100 before transmission from the IMD 100. The ECG data is stored in a leading segment 218 of an ECG memory buffer 210. The leading segment 218 has a size sufficient to store an amount of ECG data that is received over the predetermined IMD processing delay. When the predetermined EGM processing delay expires and/or the leading segment 218 of the first/ECG memory buffer 210 fills, the ED 200 begins storing the ECG data in a main segment 220 first/ECG memory buffer 210. Also, when the predetermined EGM processing delay expires and/or the leading segment 218 of the ECG memory buffer 210 fills, the ED 200 activates storage of the EGM data stream to be stored in a main segment 224 of the second/EGM memory buffer 212. The delay induced by buffering the leading segment 218 of ECG data maintains an alignment of the ECG data and EGM data as stored in the main segments 220, 224 of the first/ECG and second/EGM memory buffers 210, 212.

The ED 200 continues loading the ECG and EGM data into the main segments 220, 224 of the ECG and EGM memory buffers 210, 212 for a predetermined main buffering interval before beginning to read out ECG and EGM data for display. The predetermined main buffering interval is based on one or more characteristics of the protocol for the wireless communications path between the IMD 100 and the ED 200. For example, the predetermined main buffering interval may correspond to a maximum transmission delay, permitted by the protocol, from a last data exchange until the wireless link is declared lost. As one example, when the protocol is the BLE protocol, the predetermined main buffering interval may correspond to the BLE connection supervision timeout. By loading the ECG and EGM memory buffers for an amount to time corresponding to the BLE connection supervision timeout, all EGM data samples are delayed for a common maximum amount of time instead of some EGM data samples delayed more than the others. The maximum delay time will be the same as BLE connection supervision timeout in order that all of the EGM and ECG data are delayed by a common amount and will evenly align in the EGM and ECG memory buffers 210, 212 when read out to be displayed. When the predetermined main buffering interval times out, the ED 200 begins to read out ECG and EGM data at the same time in alignment.

In accordance with embodiments herein, methods and systems address the challenge of startup command delay by monitoring and managing an overflow segment following a trailing end of the main segment 220 of the ECG memory buffer 210. If there is an EGM startup delay then the ECG memory buffer 210 will store more ECG data than expected, in which case an appropriate amount of the first-in ECG data will be purged to re-align the ECG and EGM data in the corresponding buffers. For example, the ED 200 determines when the ECG data stream overflows the trailing end 228 of the main segment 220 of the ECG memory buffer 210. The ECG data overflows into an overflow segment 222 trailing the main segment 220. When ECG data overflows, the ED 200 "steps" or "advances" a buffer index along the stored ECG data (in the direction of arrow A in FIG. 1) from the overflow segment 222 into the main segment 220, thereby "purging" ECG data at the leading end 230 of the ECG memory buffer 210.

The ED 200 removes or skips a leading portion of the ECG data stream by an amount that is based on an amount of the overflow. For example, the overflow represents a last-in data subset of the ECG data stream that at least partially fills the overflow segment of the first/ECG memory buffer 210. The ED 200 performs a removing operation by purging, as the leading portion, a first-out data subset of the first data stream from the leading end 230 of the first/ECG memory buffer 210. The first-out data subset, that is purged, corresponds in length to a length of the last-in data subset that overflows into the overflow segment 222. The purge may include deleting or overwriting data, or advancing a current read-out index past the data to be purged, or otherwise.

In accordance with embodiments herein, methods and systems address the challenge of batched transmission. Initially, the ED 200 may manage the buffered ECG and EGM data to be streamed out of the ECG and EGM memory buffers 210, 212 for display at a first data display rate that is common with a data input rate, at which ECG and EGM data are written into the ECG and EGM buffers 210, 212. However, due to the in-deterministic nature of software process, thread performance and other factors, the data input rate varies for at least the rate at which EGM data is written to the EGM memory buffer 212. Accordingly, it is not feasible to maintain a constant data display rate.

In accordance with embodiments, methods and systems utilize a throttling technique, whereby the data display rate is initially kept as close as practical to an initial data input rate. During operation, the ED 200 monitors a size of the EGM memory buffer 212. The size of the EGM memory buffer 212 is utilized as an indication that the data input rate corresponds to "is too fast" or "is too slow" relative to the data display rate. When the EGM memory buffer 212 size grows above an upper threshold, the ED 200 increases the display date rate, at which ECG and EGM data are read out. Conversely, when the ED 200 determines that the EGM memory buffer 212 size falls below a lower threshold, the ED 200 decreases the data display rate. The ED 200 uses the throttling technique to maintain the data input within a predetermined range of the data display rate, thereby accommodating a fast or smooth flow of real-time EGM data regardless of the impact from process and thread performance variations.

Synchronization Process

Figure 2:
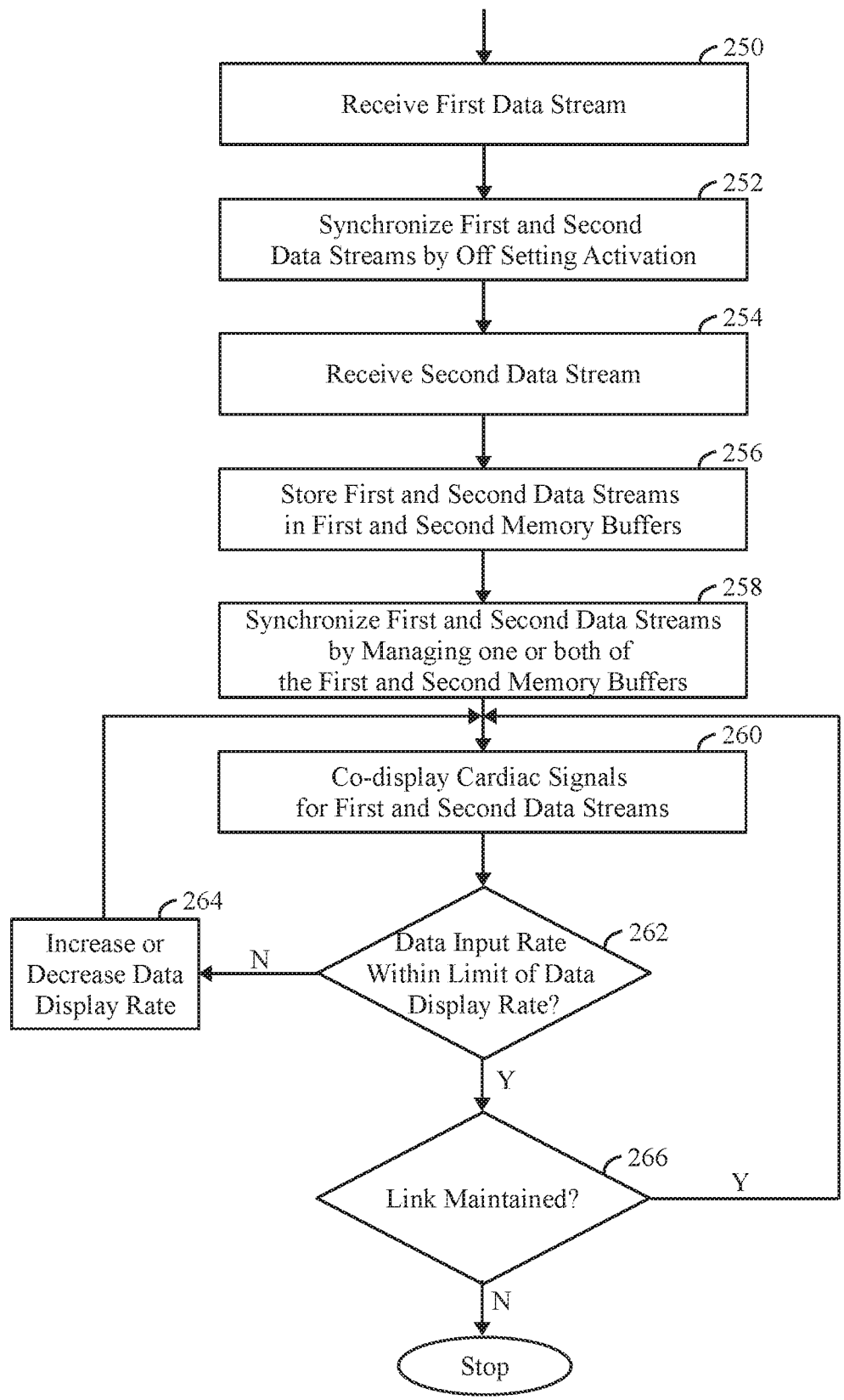
FIG. 2 illustrates a process for managing the display of cardiac signals in accordance with embodiments herein.

FIG. 2 illustrates a process for managing the display of cardiac signals in accordance with embodiments herein. The operations of FIG. 2 may be performed by one or more processors of an external device, an IMD, a server, a remote workstation, or other computing device. The operations of FIG. 2 may be distributed between one or more external device(s), an IMD, a server, a remote workstation, or other computing device.

At 250, the one or more processors receive a first data stream along a first communications path that is being conveyed with a first throughput or transfer pattern. At 252, the one or more processors synchronizes first and second data streams by temporally offsetting activation of the storing operation for the first and second data streams with respect to one another. For example, the one or more processors may manage synchronization through temporally offsetting activation of storage of the second data stream (at 254) until after activation of storage of the first data stream by a predetermined processing offset that corresponds to a processing delay introduced along the second communications path. As another example, the offsetting operation may include filling a leading segment of the first memory buffer from the first data stream before activating the storing operation for the second data stream. The leading segment has a length that corresponds to the processing delay introduced along the second communications path.

At 254, the one or more processors begin to receive the second data stream along the second communications path transmitted with second throughput. The first and second throughput are asynchronous with respect to one another. The first and second data streams carry cardiac signals sensed by external and implanted electrodes, respectively, for one or more common events. By way of example, the first and second data streams may correspond to ECG data and EGM data sensed by different ECG and EGM electrodes coupled to first and second sensing circuits, respectively. The EGM data may be conveyed along a wireless link within the second communications path and the ECG data may be conveyed along a wired link within the first communications path.

At 256, the one or more processors store the first and second data streams in first and second memory buffers. At 258, the one or more processors synchronize the first and second data streams with one another by managing an amount of the first data stream maintained in one or both of the first and second memory buffers. For example, the management operation may comprise determining when the first data stream overflows a trailing end of a main segment of the first memory buffer, and removing a leading portion of the first data stream where the amount is based on the overflow. For example, the overflow may represent a last-in data subset of the first data stream that is stored in an overflow segment of the first memory buffer. A removing operation purges, as the leading portion, a first-out data subset of the first data stream from a leading end of the first memory buffer, the first-out data subset that is purged corresponding in size/length to the size/length of the last-in data subset that overflows into the overflow segment.

Additionally or alternatively, the one or more processors may manage storage of the first and second memory buffers by writing data from the first and second data streams to the corresponding first and second memory buffers until filling a main segment of the first memory buffer from the first data stream. As one example, a size of the main segment of the first memory buffer may correspond to a maximum transmission delay (e.g., a connection supervision timeout) from a last data exchange until a link over the second communications path is declared lost. Additionally or alternatively, the one or more processors may store the first and second data streams to the first and second memory buffers for a period of time, corresponding to the connection supervision timeout, that is set in accordance with a protocol utilized for transmission over the second communications path.

At 260, the one or more processors co-display cardiac signals associated with the first and second data streams by reading the data from the first and second memory buffers at a data display rate. Data from the first and second memory buffers are read at the same data display rate, although the data display rate may be varied as explained herein. As data is read from the first and second memory buffers, a read-out index for each of the first and second memory buffers is advanced to a new data read-out point, from which data is to be read out from the corresponding memory buffer.

The cardiac signals may be co-displayed simultaneously on a common display, or alternatively simultaneously displayed on different displays located proximate to one another. The cardiac signals may be presented in various formats, such as in a graph format where the horizontal axis corresponds to time. The cardiac signals for the data read from the first and second memory buffers are arranged in a temporally aligned manner such that common events indicated within each of the cardiac signals are aligned at a common point along a timeline. The cardiac signals are continuously updated on the display at a rate corresponding to the data display rate. As explained herein, the data display rate may be varied, based on the data input rate to the memory buffers. When the data display rate is modified, the rate at which the cardiac signals are updated on the display is similarly and equally updated.

At 262-264, the one or more processors manage a read-out rate at which the first and second data streams are read from the first and second memory buffers to adjust the data display rate (e.g., throttling). For example, at 262, the one or more processors compare a size threshold to an amount of data from the second data stream that is currently loaded into the second memory buffer. The size threshold represents an indicator that the rate at which data is read from the memory buffers (e.g., the data display rate) is substantially similar to the rate at which data is written into the memory buffers (e.g., the data input rate). When an amount of data currently stored within the second memory buffer begins to increase beyond an acceptable amount above the size threshold, the one or more processors interpret the condition as an indication that the data input rate is exceeding the data display rate by an undesired amount. If left unmodified, the second memory buffer will ultimately overflow. Alternatively, when an amount of data currently stored within the second memory buffer begins to decrease beyond an acceptable amount below the size threshold, the one or more processors interpret the condition as an indication that the data input rate is falling below the data display rate by an undesired amount. If left unmodified, the second memory buffer will become empty at some point. At 264, the one or more processors adjust the data display rate based on the comparison at 262. For example, the data display rate may be increased or decreased to substantially correspond to the data input rate. Thereafter, flow returns to 262 where the cardiac signals are continued to be read out of the memory buffers and co-displayed.

Alternatively, at 262, when the data input rate is determined to remain within an acceptable range of the data display rate, flow moves to 266. At 266, the one or more processors determine whether the communications link is maintained between the ED 200 and the IMD 100. If communications link is maintained, flow returns to 260. Otherwise, when the link has been declared lost or otherwise broken, the process ends. It is recognized that the determination at 266 may be performed at other points in the process, alternatively or in addition, to determining whether the communications link is maintained.

It is recognized the operations of FIG. 2 may be performed in various orders. For example, the synchronization operations at 252 may be performed before or after receipt of the first and/or second data streams. Further, the synchronization operation at 258 is performed at an intermediate point within storage of data from one or both of the first and second data streams.

Figure 3:
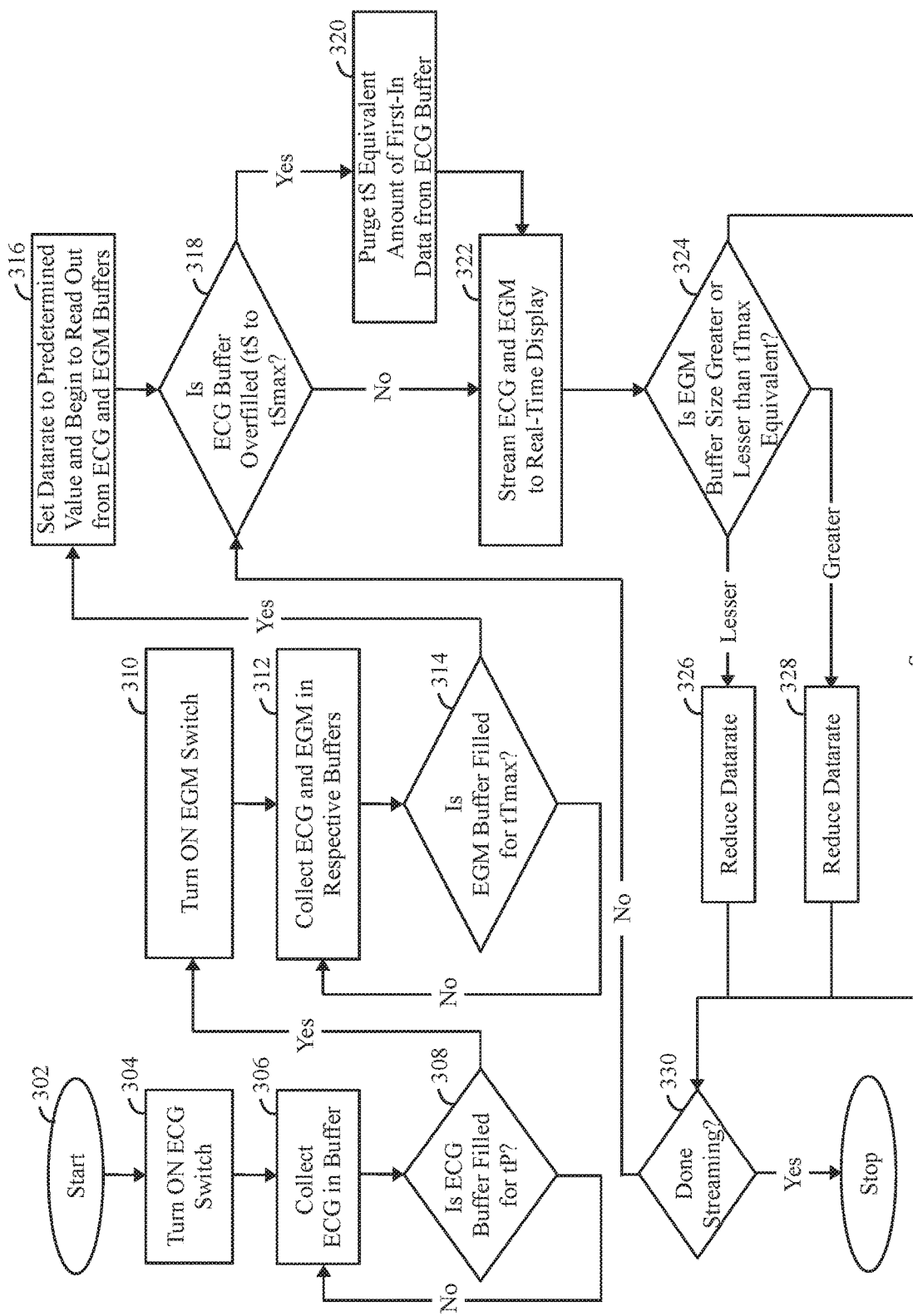
FIG. 3 illustrates a process for managing the display of cardiac signals in accordance with an embodiment herein.

FIG. 3 illustrates a process for managing the display of cardiac signals in accordance with an embodiment herein. The process of FIG. 3 may represent a more detailed illustration of the process of FIG. 2. Alternatively, the process of FIG. 2 may follow a more detailed operation flow that differs from the process of FIG. 3. The process of FIG. 3 starts at 302, where the one or more processors of the ED 200 convey a start command to the IMD 100. At 304, the one or more processors turn on receipt of ECG data that is sensed at the external electrodes. At 306, the ECG data is collected in the first/ECG memory buffer. At 308, the one or more processors determine whether the ECG memory buffer has been filled by data to a predetermined point corresponding to a IMD processing delay (denoted as tP) that corresponds to the processing delay introduced along the second communications path as EGM data is sensed and processed within the IMD 100 before transmission from the IMD 100. When the IMD processing delay is not yet reached at 308, the ECG memory buffer continues to collect additional ECG data. Once the ECG memory buffer is filled by an amount corresponding to the IMD processing delay, flow moves to 310.

At 310, the one or more processors turned on receipt of EGM data that is streamed over a wireless communications path (e.g., a BLE link) from the IMD 100. At 312, the one or more processors collect and store ECG data and EGM data that are received over the corresponding first and second communications paths. The ECG and EGM data are stored in respective ECG and EGM memory buffers. At 314, the one or more processors determine whether the EGM memory buffer has been filled for a predetermined period of time (denoted tTmax). For example, the predetermined period of time may correspond to a connection supervision timeout, and/or a maximum transmission delay that is defined by a wireless communications protocol. The ECG and EGM memory buffers continue to be filled until the predetermined period of time has elapsed at 314. Thereafter, at 316, the one or more processors set a data display rate to a predetermined value and "opens the output" of the ECG and EGM memory buffers (e.g., by beginning to read data from the ECG and EGM memory buffers). The data read from the memory buffers is provided to the display for co-display as cardiac signals.

At 318, the one or more processors determine whether a main segment of the ECG memory buffer has "overflowed." For example, the ECG memory buffer may be declared to overflow (or be overfilled) when the one or more processors determine that an amount of data within the ECG memory buffer extends past a trailing end of a main segment of the ECG memory buffer. The amount of data that overflows the trailing end of the main segment represents overflow data. The overflow data represents a "last-in data subset" of the first data stream that at least partially fills and is stored in an overflow segment of the first memory buffer. When the ECG memory buffer is determined to be overfilled, flow moves to 320, otherwise flow moves to 322.

At 320, the one or more processors remove an amount of data from the ECG memory buffer that is equal to the overflow data. In the example of FIG. 3, the overflow data is defined by a period of time tS which may vary between 0 and tSmax. Therefore, at 320, an amount of data equaling the period of time tS is removed from the leading end of the ECG memory buffer (representing a leading portion of the first data stream). The removing operation purges, as the leading portion, a first-out data subset of the ECG data stream from the leading end of the ECG memory buffer. The first-out data subset that is purged corresponds in size to a size of the last-in data subset stored in the overflow segment.

Returning to 318, when the ECG buffer is determined not to overflow, flow advances to 322. At 322, ECG and EGM data is read from the corresponding memory buffers and streamed in real time to the display simultaneously and in a time synchronized manner.

At 324 the one or more processors determine whether the EGM memory buffer size is similar, greater or less than a predetermined threshold corresponding to a maximum transmission delay tTmax. For example, the one or more processors may compare an amount of data from the EGM data stream that is currently loaded into the EGM memory buffer, with a size threshold. The size threshold represents a baseline indicator that the rate at which data is read from the EGM memory buffer (e.g., the data display rate) is substantially similar to the rate at which data is written into the EGM memory buffer (e.g., the data input rate). When an amount of data currently stored within the EGM memory buffer begins to increase beyond an acceptable amount above the size threshold, the one or more processors interpret the condition as an indication that the data input rate is exceeding the data display rate by an undesired amount. Alternatively, when an amount of data currently stored within the EGM memory buffer begins to decrease beyond an acceptable amount below the size threshold, the one or more processors interpret the condition as an indication that the data input rate is falling below the data display rate by an undesired amount. Based on the determination at 324, flow branches to 326, 328 or 330. For example, when the EGM memory buffer size is less than the predetermined threshold, flow branches to 326.

At 326, the one or more processors reduce the data display rate. At 324, when the EGM memory buffer size is greater than the predetermined threshold, flow branches to 328. At 328, the one or more processors increase the data display rate. At 324, when the EGM memory buffer size corresponds to the predetermined threshold, flow branches to 330 and the data display rate is unchanged. At 326 and 328, the data display rate may be reduced or increased in various manners. For example, the amount of change in the data display rate may correspond to a predetermined fixed increment (e.g., reducing or increasing the data display rate by a preprogrammed amount). Alternatively, the amount of change in the data display rate may be determined based on an extent to which the EGM memory buffer size exceeds or falls below the predetermined threshold. For example, when the EGM memory buffer size is greater than or less than the predetermined threshold by a significant amount or a small amount, the data display rate may similarly be reduced or increased proportionally. Optionally, the amount of change in the data display rate may be determined based on an extent to which EGM data overflows a main segment of the EGM memory buffer 212 into an EGM overflow segment 226.

At 330, the one or more processors determine whether the streaming operation should be terminated. If so, the process stops. Otherwise, flow returns to 318 where the ECG memory buffer size is again tested to identify overflow. The operations of FIG. 3 may be modified. For example, the operations at 324-328 may be removed entirely to omit the throttling process, such as when there is little or no concern that the EGM memory buffer size may vary substantially during operation. Additionally or alternatively, the operations at 318-322 may be omitted, such as when there is no concern regarding a need to synchronize based on a startup command. Additionally or alternatively, the operations at 308 and/or 314 may be omitted when there is no concern for processing delay within the IMD and/or transmission delay between the IMD and the ED.

The foregoing examples are provided primarily in connection with the use of ECG and EGM data. It is recognized that other types of data may be collected from a patient in real time in place of or in addition to ECG and EGM data, where the additional types of data are also related to a common event. For example, sensors may be utilized to record heart sounds, with heart sound data provided along a corresponding heart sound communications path for display synchronized in time with ECG data, EGM data and/or another type of data. As another example, sensors may be utilized to record impedance, with impedance data provided along a corresponding impedance communications path for display synchronized with the other types of data described herein.

The foregoing examples are described in connection with utilizing a Bluetooth communications protocol as one example. It is recognized that other asynchronous pocket and burst type communications protocols may be utilized for wireless communication between an IMD and an external device. Additionally or alternatively, the ECG electrodes may convey ECG data over a wired or wireless communications link. For example, the ECG electrodes may be connected to an ECG monitor that is separate and apart from the external device that wirelessly communicates with an IMD. In this alternative example, the ECG monitor may transmit ECG signals wirelessly (or wired) to the external device 200. When a separate ECG monitor is utilized, the external device 200 may adjust the values for the various thresholds described herein in connection with processing timing, transmission timing, buffer overflow, and/or throttling.

Figure 4:
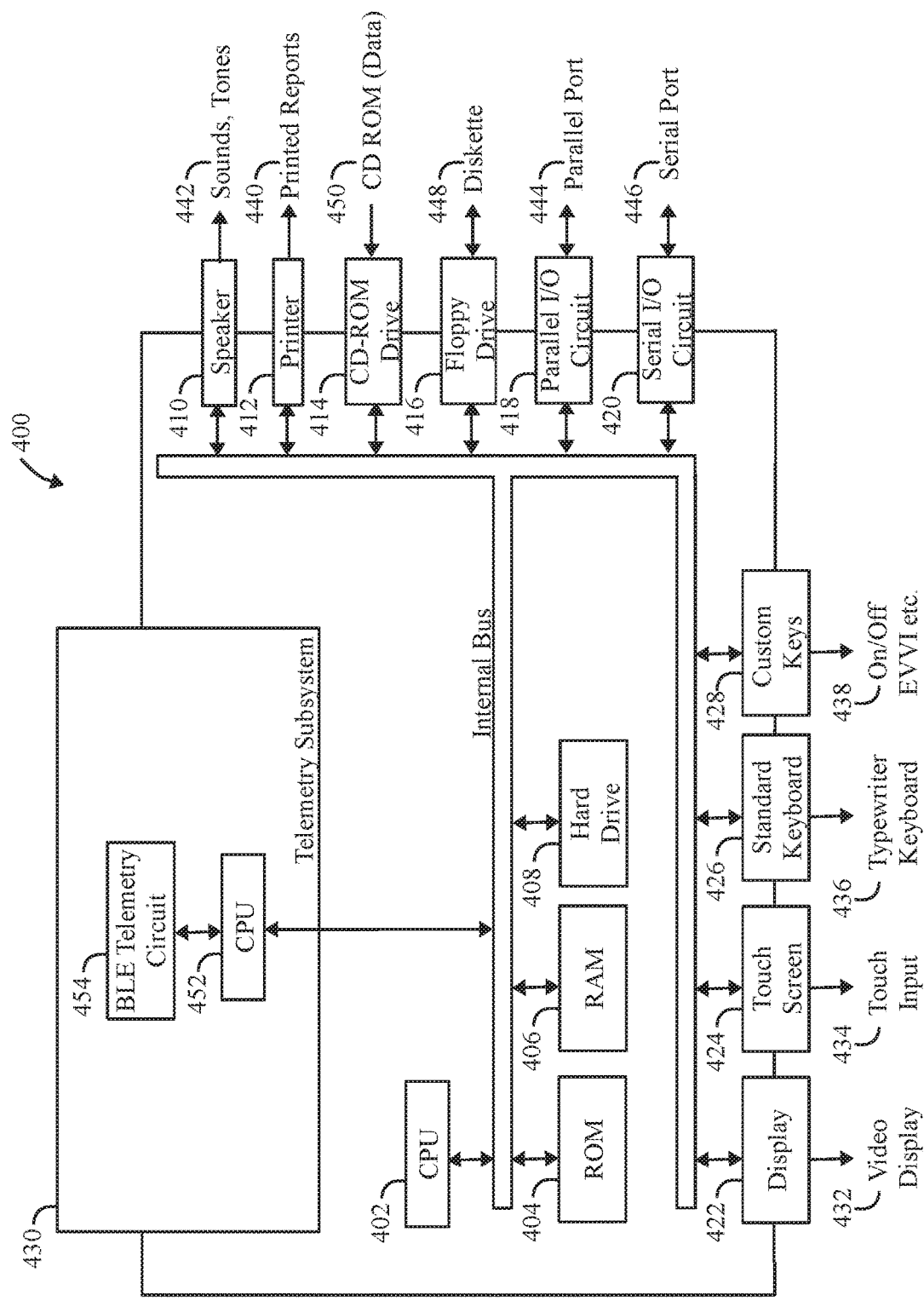
FIG. 4 illustrates a functional block diagram of an external device 400 that is operated in accordance with the processes described herein and to interface with implantable medical devices as described herein.

FIG. 4 illustrates a functional block diagram of an external device 400 that is operated in accordance with the processes described herein and to interface with implantable medical devices as described herein. The external device 400 may be a bedside monitor, a workstation, a portable computer, an IMD programmer, a PDA, a cell phone and the like, that includes all or a portion of the structures described hereafter. The external device 400 implements the memory buffers, switching operations, delays and other processing operations described above in connection with FIG. 1.

The external device 400 includes an internal bus that connects/interfaces with a Central Processing Unit (CPU) 402, ROM 404, RAM 406, a hard drive 408, the speaker 410, a printer 412, a CD-ROM drive 414, a floppy drive 416, a parallel I/O circuit 418, a serial I/O circuit 420, the display 422, a touch screen 424, a standard keyboard connection 426, custom keys 428, and a telemetry subsystem 430. The internal bus is an address/data bus that transfers information between the various components described herein. The hard drive 408 may store operational programs as well as data, such as waveform templates and detection thresholds. The RAM 406 stores data from the ECG/first and EGM/second data streams in first and second memory buffers (also referred to as ECG and EGM memory buffers). Optionally, the first and second memory buffers may be implemented in other types of memory, and/or in cache of the CPU 402, 452.

The CPU 402 typically includes a microprocessor, a micro-controller, or equivalent control circuitry, designed specifically to control interfacing with the external device 400 and with the IMD 100. The CPU 402 performs the processes discussed herein. The CPU 402 may include RAM or ROM memory, logic and timing circuitry, state machine circuitry, and I/O circuitry to interface with the IMD 100. The display 422 (e.g., may be connected to the video display 432). The touch screen 424 displays graphic information relating to the IMD 100. The display 422 displays various information related to the processes described herein, including co-display of traces of ECG and EGM cardiac signals over time. The display 422 co-displays cardiac signals associated with the first and second data stream under the control of the CPU which reads the data from the first and second memory buffers at a data display rate.

The touch screen 424 accepts a user's touch input 434 when selections are made. The keyboard 426 (e.g., a typewriter keyboard 436) allows the user to enter data to the displayed fields, as well as interface with the telemetry subsystem 430. Furthermore, custom keys 428 turn on/off 438 (e.g., EVVI) the external device 400. The printer 412 prints copies of reports 440 for a physician to review or to be placed in a patient file, and speaker 410 provides an audible warning (e.g., sounds and tones 442) to the user. The parallel I/O circuit 418 interfaces with a parallel port 444. The serial I/O circuit 420 interfaces with a serial port 446. The serial or parallel I/O circuits 420, 418 may be coupled to one or more ECG leads or other surface electrodes to form an ECG/first input to receive a first/ECG data steam along a first communications path conveyed in accordance with a first throughput.

The telemetry subsystem 430 includes a central processing unit (CPU) 452 in electrical communication with a telemetry circuit 454. The telemetry circuit 454 wirelessly communicates with an IMD based on a wireless communications protocol, such as the BLE protocol. The telemetry circuit 454 represents an EGM/second input that receives a second data stream along a second communications path transmitted in accordance with a second throughput. The first and second throughputs are asynchronous with respect to one another. The first and second data streams carrying cardiac signals sensed by the external ECG lead and implanted electrodes, respectively, for one or more common events. The ECG/first throughput represents even and continuous, and the EGM/second throughput represents intermittent bursts.

The telemetry circuit 454 includes a receiver that may be configured to communicate with an IMD to receive EGM data as the second data stream from the IMD in accordance with a Bluetooth Low Energy transmission protocol or another burst type wireless protocol.

The CPU 402, when executing program instructions, synchronize the data stored in the first and second memory buffers with one another by performing at least one of: i) temporally offsetting activation of the storing operation for the first and second data streams with respect to one another; or ii) managing an amount of the data maintained in at least one of the first memory buffer or the second memory buffer. The CPU 402 compares an amount of data from the second data stream loaded into the second memory buffer with a size threshold of the second memory buffer, and adjusts the data display rate based on the comparing operation. When the CPU 402 manages the amount of data maintained in the ECG/first memory buffer, the CPU 402 determines when the first data stream overflows a trailing end of a main segment of the first memory buffer and removing a leading portion of the first data stream by an amount based on the overflow. For example, the overflow represents a last-in data subset of the first data stream that is stored in an overflow segment of the first memory buffer. The CPU 402 purges, as the leading portion, a first-out data subset of the first data stream from a leading end of the first memory buffer, the first-out data subset that is purged corresponding in length to a length of the last-in data subset that overflows into the overflow segment. The CPU 402 performs an offsetting operation which includes offsetting activation of storage of the second data stream until after activation of storage of the first data stream by a predetermined processing offset that corresponds to a processing delay introduced along the second communications path. Optionally, the CPU 402 may offset by filling a leading segment of the first memory buffer from the first data stream before activating the storing operation for the second data stream, the leading segment corresponding to a processing delay introduced along the second communications path.

The floppy drive 416 accepts diskettes 448. Optionally, the floppy drive 416 may include a USB port or other interface capable of communicating with a USB device such as a memory stick. The CD-ROM drive 414 accepts CD ROMs 450. The external device 400 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 400 to the IMD 100.

Implantable Medical Device

Figure 5:
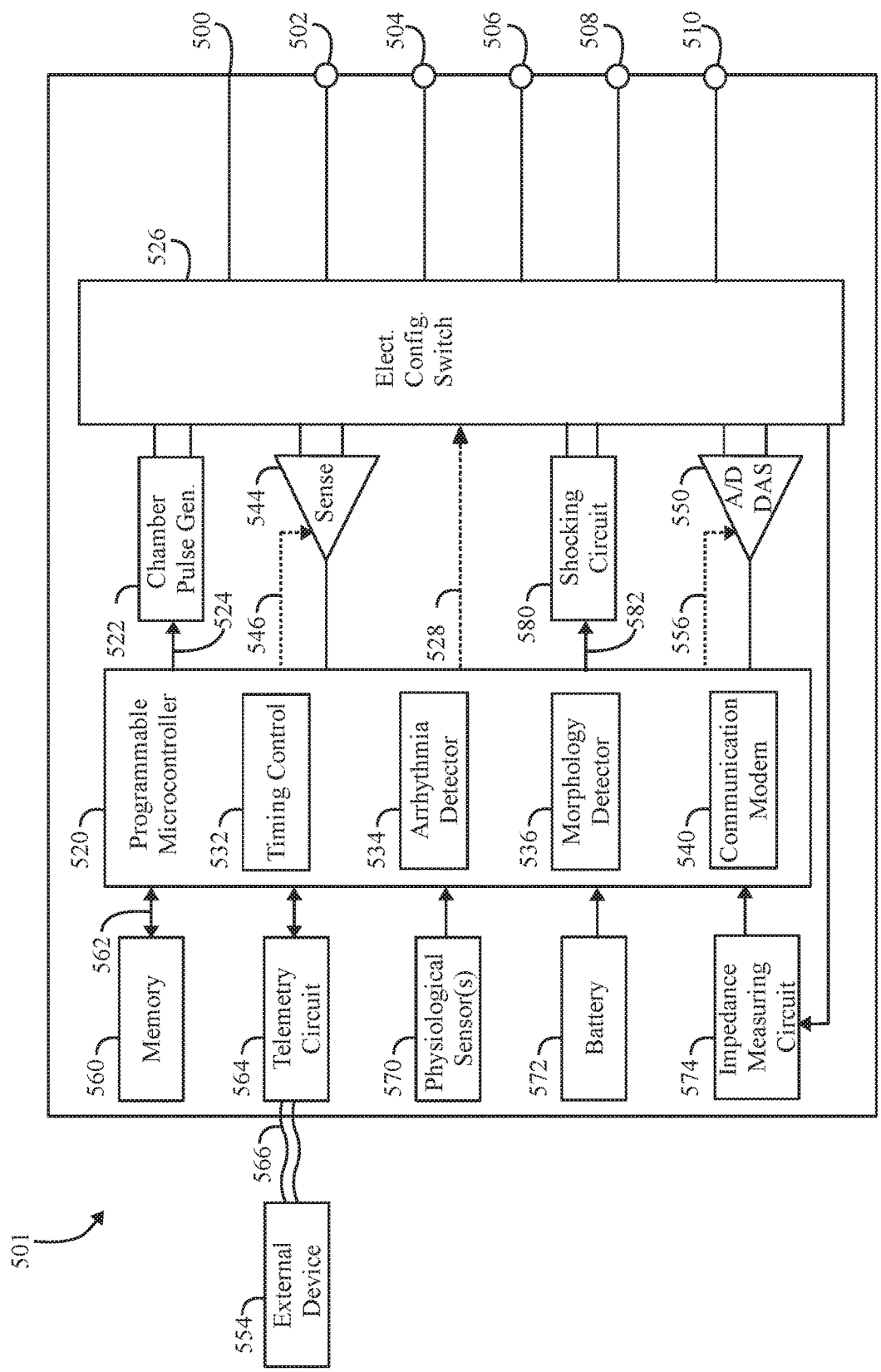
FIG. 5 shows an exemplary IMD that is implanted into the patient as part of the implantable cardiac system.

FIG. 5 shows an exemplary IMD 500 that is implanted into the patient as part of the implantable cardiac system. The IMD 500 may be implemented as a full-function biventricular pacemaker, equipped with both atrial and ventricular sensing and pacing circuitry for four chamber sensing and stimulation therapy (including both pacing and shock treatment). Optionally, the IMD 500 may provide full-function cardiac resynchronization therapy. Alternatively, the IMD 500 may be implemented with a reduced set of functions and components. For instance, the IMD may be implemented without ventricular sensing and pacing.

The IMD 500 has a housing 501 to hold the electronic/computing components. The housing 501 (which is often referred to as the "can", "case", "encasing", or "case electrode") may be programmably selected to act as the return electrode for certain stimulus modes. Housing 501 further includes a connector (not shown) with a plurality of terminals 502, 504, 506, 508, and 510. The terminals may be connected to electrodes that are located in various locations within and about the heart. For example, the terminals may include: a terminal 502 to be coupled to an first electrode (e.g., a tip electrode) located in a first chamber; a terminal 504 to be coupled to a second electrode (e.g., tip electrode) located in a second chamber; a terminal 506 to be coupled to an electrode (e.g., ring) located in the first chamber; a terminal 508 to be coupled to an electrode located (e.g., ring electrode) in the second chamber; and a terminal 510 to be coupled to an electrode (e.g., coil) located in the SVC. The type and location of each electrode may vary. For example, the electrodes may include various combinations of ring, tip, coil and shocking electrodes and the like.

The IMD 500 includes a programmable microcontroller 520 that controls various operations of the IMD 500, including cardiac monitoring and stimulation therapy. Microcontroller 520 includes a microprocessor (or equivalent control circuitry), RAM and/or ROM memory, logic and timing circuitry, state machine circuitry, and I/O circuitry.

IMD 500 further includes a first chamber pulse generator 522 that generates stimulation pulses for delivery by one or more electrodes coupled thereto. The pulse generator 522 is controlled by the microcontroller 520 via control signal 524. The pulse generator 522 is coupled to the select electrode(s) via an electrode configuration switch 526, which includes multiple switches for connecting the desired electrodes to the appropriate I/O circuits, thereby facilitating electrode programmability. The switch 526 is controlled by a control signal 528 from the microcontroller 520.

In the example of FIG. 5, a single pulse generator 522 is illustrated. Optionally, the IMD 500 may include multiple pulse generators, similar to pulse generator 522, where each pulse generator is coupled to one or more electrodes and controlled by the microcontroller 520 to deliver select stimulus pulse(s) to the corresponding one or more electrodes.

Microcontroller 520 is illustrated to include timing control circuitry 532 to control the timing of the stimulation pulses (e.g., pacing rate, atrio-ventricular (AV) delay, atrial interconduction (A-A) delay, or ventricular interconduction (V-V) delay, etc.). The timing control circuitry 532 may also be used for the timing of refractory periods, blanking intervals, noise detection windows, evoked response windows, alert intervals, marker channel timing, and so on. Microcontroller 520 also has an arrhythmia detector 534 for detecting arrhythmia conditions and a morphology detector 536 to review and analyze one or more features of the morphology of cardiac signals. Although not shown, the microcontroller 520 may further include other dedicated circuitry and/or firmware/software components that assist in monitoring various conditions of the patient's heart and managing pacing therapies.

The IMD 500 is further equipped with a communication modem (modulator/demodulator) 540 to enable wireless communication with other devices, implanted devices and/or external devices. In one implementation, the communication modem 540 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 540 may be implemented in hardware as part of the microcontroller 520, or as software/firmware instructions programmed into and executed by the microcontroller 520. Alternatively, the modem 540 may reside separately from the microcontroller as a standalone component.

The IMD 500 includes sensing circuitry 544 selectively coupled to one or more electrodes that perform sensing operations, through the switch 526 to detect the presence of cardiac activity in the right chambers of the heart. The sensing circuitry 544 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit 502 to sense low amplitude signal characteristics of atrial fibrillation. Switch 526 determines the sensing polarity of the cardiac signal by selectively closing the appropriate switches. In this way, the clinician may program the sensing polarity independent of the stimulation polarity.

The output of the sensing circuitry 544 is connected to the microcontroller 520 which, in turn, triggers or inhibits the pulse generator 522 in response to the absence or presence of cardiac activity. The sensing circuitry 544 receives a control signal 546 from the microcontroller 520 for purposes of controlling the gain, threshold, polarization charge removal circuitry (not shown), and the timing of any blocking circuitry (not shown) coupled to the inputs of the sensing circuitry.

In the example of FIG. 5, a single sensing circuit 544 is illustrated. Optionally, the IMD 502 may include multiple sensing circuit, similar to sensing circuit 544, where each sensing circuit is coupled to one or more electrodes and controlled by the microcontroller 520 to sense electrical activity detected at the corresponding one or more electrodes. The sensing circuit 544 may operate in a unipolar sensing configuration or in a bipolar sensing configuration.

The IMD 500 further includes an analog-to-digital (A/D) data acquisition system (DAS) 550 coupled to one or more electrodes via the switch 526 to sample cardiac signals across any pair of desired electrodes. The data acquisition system 550 is configured to acquire intracardiac electrogram signals, convert the raw analog data into digital data, and store the digital data for later processing and/or telemetric transmission to an external device 554 (e.g., a programmer, local transceiver, or a diagnostic system analyzer). The data acquisition system 550 is controlled by a control signal 556 from the microcontroller 520. The microcontroller 520 processes EGM data received from the data acquisition system 550 and transmits the EGM data to the external device 554. The data acquisition system 550 and microcontroller 520 introduce certain processing delays between the time that the EGM signals are sensed and the EGM data is transmitted.

The microcontroller 520 is coupled to a memory 560 by a suitable data/address bus 562. The programmable operating parameters used by the microcontroller 520 are stored in memory 560 and used to customize the operation of the IMD 500 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the IMD 500 may be non-invasively programmed into the memory 560 through a telemetry circuit 564 in telemetric communication via communication link 566 with the external device 554. The telemetry circuit 564 allows intracardiac electrograms and status information relating to the operation of the IMD 500 (as contained in the microcontroller 520 or memory 560) to be sent to the external device 554 through the established communication link 566. As explained herein, the IMD 500 transmits EGM data to the external device 400 in accordance with a wireless protocol related to the communications link. For example, the telemetry circuit 564 may utilize a BLE protocol to transmit EGM data in a burst type manner having an un-even throughput.

The IMD 500 can further include magnet detection circuitry (not shown), coupled to the microcontroller 520, to detect when a magnet is placed over the unit. A magnet may be used by a clinician to perform various test functions of the unit 500 and/or to signal the microcontroller 520 that the external device 554 is in place to receive or transmit data to the microcontroller 520 through the telemetry circuits 564.

The IMD 500 can further include one or more physiologic sensors 570. Such sensors are commonly referred to as "rate-responsive" sensors because they are typically used to adjust pacing stimulation rates according to the exercise state of the patient. However, the physiological sensor 570 may further be used to detect changes in cardiac output, changes in the physiological condition of the heart, or diurnal changes in activity (e.g., detecting sleep and wake states). Signals generated by the physiological sensors 570 are passed to the microcontroller 520 for analysis. The microcontroller 520 responds by adjusting the various pacing parameters (such as rate, AV Delay, V-V Delay, etc.) at which the atrial and ventricular pacing pulses are administered. While shown as being included within the unit 500, the physiologic sensor(s) 570 may be external to the unit 500, yet still be implanted within or carried by the patient. Examples of physiologic sensors might include sensors that, for example, sense respiration rate, pH of blood, ventricular gradient, activity, position/posture, minute ventilation (MV), and so forth.

A battery 572 provides operating power to all of the components in the IMD 500. The battery 572 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 572 also desirably has a predictable discharge characteristic so that elective replacement time can be detected. As one example, the unit 500 employs lithium/silver vanadium oxide batteries.

The IMD 500 further includes an impedance measuring circuit 574, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 574 is coupled to the switch 526 so that any desired electrode may be used.

The IMD 500 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 520 further controls a shocking circuit 580 by way of a control signal 582. The shocking circuit 580 generates shocking pulses of low (e.g., up to 0.5 joules), moderate (e.g., 0.5-10 joules), or high energy (e.g., 511 to 40 joules), as controlled by the microcontroller 520. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A system to manage display of cardiac signals, the system comprising:
   a first input to receive a first data stream along a first communications path conveyed in accordance with a first throughput;
   a second input to receive a second data stream along a second communications path transmitted in accordance with a second throughput, the first and second throughput asynchronous with respect to one another, the first and second data streams carrying cardiac signals sensed by external and implanted electrodes, respectively, for one or more common events;
   memory to store data from the first and second data streams in first and second memory buffers;
   one or more processors that, when executing program instructions, synchronize the data stored in the first and second memory buffers with one another by performing at least one of:
   i) temporally offsetting activation of the storing operation for the first and second data streams with respect to one another; or
   ii) managing an amount of the data maintained in at least one of the first memory buffer or the second memory buffer; and
   a display to co-display cardiac signals associated with the first and second data stream by reading the data from the first and second memory buffers at a data display rate.

2. The system of claim 1, further comprising a sensing circuit connected to the first input, the first input configured to be connected to one or more ECG leads having ECG electrodes to sense ECG data as the first data stream.

3. The system of claim 1, further comprising a receiver connected to the second input, the receiver configured to communicate with an IMD to receive EGM data as the second data stream from the IMD in accordance with a Bluetooth Low Energy transmission protocol.

4. The system of claim 1, wherein the first throughput represents even and continuous, and wherein the second throughput represents intermittent bursts.

5. The system of claim 1, further comprising comparing an amount of data from the second data stream loaded into the second memory buffer with a size threshold of the second memory buffer; and adjusting the data display rate based on the comparing operation.

6. The system of claim 1, wherein the synchronizing operation performs the managing operation, the system further comprising determining when the first data stream overflows a trailing end of a main segment of the first memory buffer; and removing a leading portion of the first data stream by an amount based on the overflow.

7. The system of claim 6, wherein the overflow represents a last-in data subset of the first data stream that is stored in an overflow segment of the first memory buffer; and the removing operation purges, as the leading portion, a first-out data subset of the first data stream from a leading end of the first memory buffer, the first-out data subset that is purged corresponding in length to a length of the last-in data subset that overflows into the overflow segment.

8. The system of claim 1, wherein the synchronizing operation performs the offsetting operation which includes offsetting activation of storage of the second data stream until after activation of storage of the first data stream by a predetermined processing offset that corresponds to a processing delay introduced along the second communications path.

9. The system of claim 1, wherein the synchronizing operation performs the offsetting operation which includes filling a leading segment of the first memory buffer from the first data stream before activating the storing operation for the second data stream, the leading segment corresponding to a processing delay introduced along the second communications path.

* * * * *